United States Patent

Renko et al.

[11] Patent Number: 5,958,903
[45] Date of Patent: Sep. 28, 1999

[54] GALANTHAMINE DERIVATIVES, AND THEIR PHARMACEUTICAL COMPOSITIONS

[75] Inventors: Dolor Renko, Gif-sur-Yvette; Pierre Potier; Yves Christen, both of Paris; Claude Thal, Sceaux; Catherine Guillou, Gifsur-Yvette; Aude Mary, Draveil, all of France

[73] Assignee: Societe de Conseils de Recherches et D'Applications Scientifiques (S.C.R.A.S.), France

[21] Appl. No.: 08/983,309

[22] PCT Filed: Jul. 19, 1996

[86] PCT No.: PCT/FR96/01139

§ 371 Date: Jan. 9, 1998

§ 102(e) Date: Jan. 9, 1998

[87] PCT Pub. No.: WO97/03987

PCT Pub. Date: Feb. 6, 1997

[30] Foreign Application Priority Data

Jul. 19, 1995 [GB] United Kingdom ............... 9514821

[51] Int. Cl.⁶ .................. C07D 491/08; A01N 57/00; A61K 31/55
[52] U.S. Cl. .................. 514/80; 514/215; 540/581
[58] Field of Search ............... 540/581; 514/215, 514/80

[56] References Cited

U.S. PATENT DOCUMENTS

| | | | |
|---|---|---|---|
| 4,663,318 | 5/1987 | Davis | 514/215 |
| 5,428,159 | 6/1995 | Shieh et al. | 540/581 |
| 5,589,475 | 12/1996 | Snorrason | 514/215 |
| 5,633,238 | 5/1997 | Snorrason | 514/80 |

FOREIGN PATENT DOCUMENTS

| | | |
|---|---|---|
| 0653427 | 5/1995 | European Pat. Off. . |
| PCT/US8801542 | 5/1988 | WIPO . |

OTHER PUBLICATIONS

Chemical Abstracts, vol.115,No. 1, Jul. 8, 1991, C.Paul Bianchi Helvetica Chimica Acta vol. 77 (1–94) pp. 1611–1615.

Primary Examiner—John M. Ford
Assistant Examiner—Pavanaram K Sripada
Attorney, Agent, or Firm—Bierman, Muserlian and Lucas

[57] ABSTRACT

Novel galanthamine derivatives of general formulae (Ia) and (Ib), a method for preparing same, pharmaceutical compositions containing said derivatives, and their use, in particular as cholinesterase inhibitors, are disclosed.

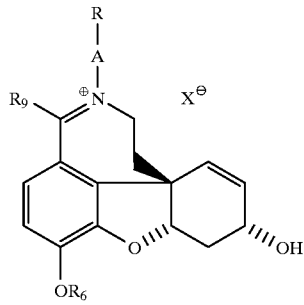

(Ia)

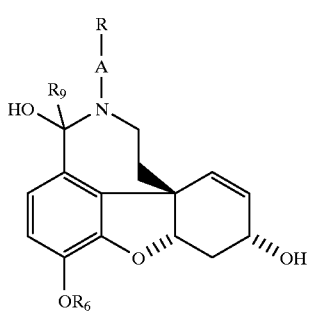

(Ib)

5 Claims, No Drawings

GALANTHAMINE DERIVATIVES, AND THEIR PHARMACEUTICAL COMPOSITIONS

This application is a 371 of PCT/FR96/01134 Jul. 14, 1996.

The present invention concerns novel galanthamine derivatives, a procedure for their preparation, pharmaceutical compositions comprising them and their use notably as cholinesterase inhibitors.

A certain number of cholinesterase inhibitors are used clinically as antagonists of neuromuscular blocking induced by nondepolarized muscular relaxants so as to palliate diverse anomalies linked to cholinergic transmission such as maintenance of muscle force in patients suffering from myasthenia gravis or in the treatment of glaucoma. For several years, pharmacological studies of cholinesterase inhibitors have been developed extensively, leading to the perfection for use of such medications as tacrine. This compound reduces the symptoms of Alzheimer's disease that results from a progressive neurodegenerative process characterized by short and long-term memory loss, cognitive functions and intellectual performances. Among these inhibitors, galanthamine of formula

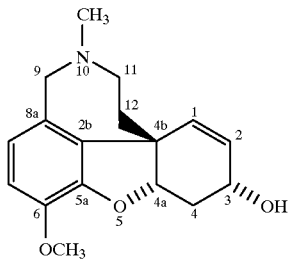

is well known. It is an alkaloid from the family of Amaryllidaceae that was isolated from snowdrop Galanthus Nivalis. This alkaloid is a reversible inhibitor of acetylcholinesterase and is generally used in the treatment of neurodegenerative diseases and, more recently, of the Alzheimer type senile dementias. Galanthamine bromohydrate is used clinically under the commercial name Nivaline™

The invention has thus as its object products of the general formula Ia:

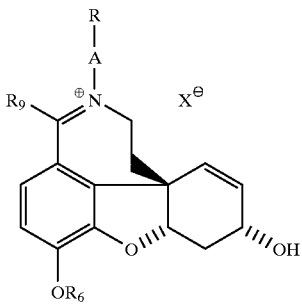

in which

A represents a linear or branched alkylene group, saturated or unsaturated, comprising from 1 to 12 carbon atoms;
R represents a hydrogen atom or a group of formula —NR'R" or —N⊕R'R"R'" in which
R' and R" represent, independently, a hydrogen atom; a cyano radical; alkyl arylalkyl; arylalkenyl; alkylcarbo-nyl or arylcarbonyl, the alkyl, alkylenyl and aryl radicals potentially being substituted by one or more identical or different radicals chosen from among the halo, hydroxy, alkoxy, alkylthio, acyl, free carboxy, salified or esterified, cyano, nitro, mercapto, or amino radicals, the amino radical potentially itself being substituted by one or more identical or different alkyl radicals; or R' and R" are bonded and, with the nitrogen atom to which they are attached, form a heterocycle;

R'" represents a hydrogen atom, a cyano radical, alkyl, arylalkyl, arylalkenyl, alkylcarbonyl, or arylcarbonyl, the alkyl, alkylenyl and aryl radicals potentially being substituted by one or more identical or different radicals chosen from among the halo, hydroxy, alkoxy, alkylthio, acyl, free carboxy, salified or esterified, cyano, nitro, mercapto or amino radicals, the amino radical potentially being itself substituted by one or more identical or different alkyl radicals;

$R_6$ represents a hydrogen atom or a radical of formula —A—R in which A and R have the significance indicated above;

$R_9$ represents a hydrogen atom or a radical of formula $R'_9$ in which $R'_9$ represents a linear or branched alkyl radical or a linear and branched alkenyl radical, the alkyl and alkenyl radicals potentially being substituted by one or more identical or different radicals chosen from among the halo; hydroxy; alkoxy; alkylthio; acyl; free carboxy, salified or esterified; cyano; nitro; mercapto; amino of formula —NR'R" in which R' and R" are as defined above; cycloalkyl or aryl, the cycloalkyl and aryl radicals potentially themselves being substituted by one or more identical or different radicals chosen from among the halo, hydroxy, alkyl, alkenyl, haloalkyl, alkoxy, alkylthio, acyl, free carboxy, salified or esterified, cyano, nitro or amino radicals potentially being substituted by one or more identical or different alkyl radicals;

$X^-$ represents a pharmaceutically acceptable anion.

The pharmaceutically acceptable $X^-$ anion may be formed by organic or inorganic acids, such as hydrochloric, hydrobromic, sulfuric, phosphoric, acetic, trifluoroacetic, citric, propionic, malonic, succinic, fumaric, tartaric, cinnamic, methanesulfonic and p-toluene-sulfonic acids.

At specific pH-values the product of formula Ia, as defined above is, in equilibrium with the product corresponding to formula Ib

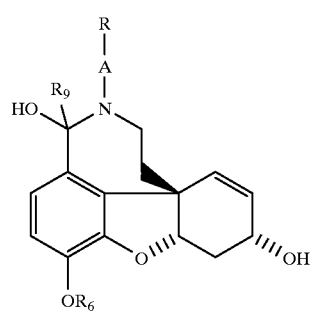

in which R, A, $R_6$, and $R_9$, have the significance indicated above, according to the following diagram:

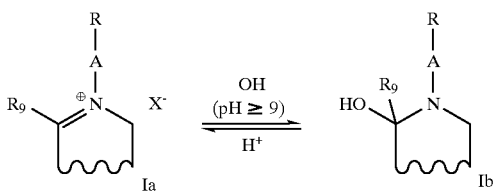

The existence of this equilibrium according to the pH-value may be of interest in order to travers the biological barriers according to the method of administration used.

The invention has as object as well products of formula Ib, such as defined above, in addition to the salts of these products.

In the expressions indicated above, the term halo represents a fluoro, chloro, bromo or iodo radical, preferably bromo.

The saturated alkylene term designates a hydrocarbon chain, linear (polymethylene) or branched, comprised of 1 to 12 carbons. Thus the alkylene term may designate the methylene, ethylene, propylene, butylene, pentylene (pentamethylene), hexylene (hexamethylene), heptylene, octylene, nonanylene, decanylene, undecanylene and dodecanylene radicals.

Unsaturated alkylene groups mean groupings comprising one or more double bonds and/or several triple bonds.

It is understood in particular that these groups comprise one or more double bonds and in particular the alkenylene groups comprising a double bond, such as the vinylene group (or ethenylene) or the propenylene group. It is understood as well that these groups comprise one or more triple bonds and in particular the alkynylene groups comprising a triple bond such as ethynylene or propynylene.

These different groups may be branched as well. For example, the ethylethylene group, the formula $CH_3CHCH_2$— group or 4-propyl-2-pentenylene group may be cited.

The term alkyl designates a linear or branched alkyl radical comprising from 1 to 12 carbon atoms. Preferably, the alkyl term represents a linear or branched alkyl radical comprising from 1 to 6 carbon atoms and in particular the methyl, ethyl, propyl, isopropyl, butyl, isobutyl, sec-butyl and tert-butyl, pentyl, isopentyl, hexyl and isohexyl radicals.

The term alkenyl designates a linear or branched alkenyl radical comprising from 1 to 12 carbon atoms. The term alkenyl represents preferably a linear or branched alkenyl radical comprising from 1 to 6 carbon atoms and in particular the vinyl, allyl, propenyl, butenyl, pentenyl, or hexenyl radicals.

The term haloalkyl designates preferably an alkyl radical such as defined above and substituted by one or more halogen atoms as defined above such as, for example, bromoethyl, trifluoromethyl, trifluoroethyl or even pentafluoroethyl.

The term alkylthio designates the radicals in which the alkyl radical has the significance indicated above. Preferably, the alkylthio term represents a methylthio, ethylthio, propylthio, butylthio or pentylthio radical.

The alkoxy radicals designate radicals in which the alkyl radical has the significance indicated above. The methoxy, ethoxy, isopropyloxy, or tert-butyloxy radicals are prefered.

The expression cycloalkyl designates a cycloalkyl, saturated or unsaturated, with 3 to 7 carbon atoms. The saturated cycloalkyl radicals may be chosen from among the cyclopropyl, cyclobutyl, cyclopentyl, cyclohexyl or cycloheptyl radicals. The unsaturated cycloalkyl radicals may be chosen from among the cyclobutene, cyclopentene, cyclohexene, cyclopentanediene or cyclohexadiene radicals.

The expression amino, potentially substituted by one or more identical or different alkyl radicals, represents the amino radical potentially substituted by one or more of the alkyl radicals as defined above. Preferably, this expression designates the amino radical, the monoalkylamino radicals, such as methylamino or ethylamino, or dialkylarmino such as dimethylamino or diethylamino.

The expression heterocycle designates a saturated or unsaturated heterocycle, monocyclic or polycyclic, potentially substituted and comprising from 3 to 9 carbon atoms and at least one nitrogen atom. The heterocycle may comprise several identical or different heteroatoms. Preferably, these heteroatoms are chosen from among oxygen, sulfur or nitrogen. Examples of heterocycles are the pyrrole, imidazole, isothiazole, thiazole, isoxazole, oxazole, pyridine, pyrazine, pyrimidine, pyridazine, indole, isoindole, indazole, quinoline, isoquinoline, phthalazine, quinazoline, pyrrolidine, imidazolidine, pyrrazolidine, piperidine, piperazine, morpholine, thiazolidine or phthalimide.

The expression acyl designates an acyl radical comprising from 1 to 6 carbon atoms such as, for example, the formyl, acetyl, propionyl, butyryl, pentanoyl, hexanoyl, acryloyl, crotonoyl or benzoyl radical.

The expression aryl represents an unsaturated radical, comprised of one cycle or of condensed cycles: each cycle may potentially contain one or more identical or different heteroatoms chosen from among sulfur, nitrogen or oxygen. Some examples of the aryl radical are phenyl, naphtyl, thienyl, furyl, pyrrolyl, imidazolyl, pyrazolyl, isothiazole, thiazole, isoxazolyl, oxazole, pyridyl, pyrazyl, pyrimidyl, benzothienyl, benzofuryl, indolyl.

The invention has as its object particularly compounds of general formula Ia or Ib such as defined above, in which A represents a linear or branched alkylene, alkenylene or alynylene group comprising from 1 to 8 carbon atoms;

R represents a hydrogen atom or a group of formula —NR'R" or $N^{\oplus}R'R"R'''$ in which R' and R" represent, independently, a hydrogen atom, a cyano radical, alkyl, arylalkyl, arylalkenyl, alkycarbonyl or arylcarbonyl, the alkyl, alkylenyl and aryl radicals potentially being substituted by one or more identical or different radicals chosen from among the halo, hydroxy, methoxy, ethoxy, isopropyloxy, tert-butyloxy, methylthio, ethylthio, propylthio, butylthio, pentylthio, formyl, acetyl, propionyl, butyryl, pentanoyl hexanoyl, acryloyl, crotonoyl, benzoyl, free or esterified carboxy, cyano, nitro, mercapto, amino, methylamino, ethylamino, dimethylamino or diethylamino radicals; or R' and R" are bonded and form, with the nitrogen atom to which they are attached, a pyrrole radical, imidazole, isothiazole, thiazole, isoxazole, oxazole, pyridine, pyrazine, pyrimidine, pyridazine, indole, isoindole, indazole, quinoline, isoquinoline, phthalazine, quinazoline, pyrrolidine, imidazolidine, pyrrazolidine, piperidine, piperazine, morpholine, thiazolidine or phthalimide; R''' represents a hydrogen atom, a cyano, alkyl, arylalkyl, arylalkenyl, alkylcarbonyl or arylcarbonyl radical, the alkyl, alkylenyl and aryl radicals potentially being substituted by one or more identical or different radicals chosen from among the halo, hydroxy, methoxy, ethoxy, isopropyloxy, tert-butyloxy, methylthio, ethylthio, propylthio, butylthio, pentylthio, formyl, acetyl, propionyl, butyryl, pentanoyl, hexanoyl, acryloyl, crotonoyl, benzoyl, free or esterified carboxy, cyano, nitro, mercapto, amino, methylamino, ethylamino, dimethylamino or diethylamino;

$R_6$ represents a hydrogen atom or a radical of formula —A—R in which A and R have the significance indicated above;

$R_9$ represents a hydrogen atom or a radical of formula $R'_9$ in which $R'_9$ represents an alkyl radical, linear or branched, or alkenyl, linear or branched, the alkyl and alkenyl radicals potentially being substituted by one or more identical or different radicals chosen from among the halo, hydroxy, methoxy, ethoxy, isopropyloxy, tert-butyloxy, methylthio, ethylthio, propylthio, butylthio, pentylthio, formyl, acetyl, propionyl, butyryl, pentanoyl, hexanoyl, acryloyl, crotonoyl, benzoyl, free or esterified carboxy, cyano, nitro, mercapto, amino, methylamino, ethylamino, dimethylamino, diethylamino radicals or the cyclopropyl, cyclobutyl, cyclopentyl, cyclohexyl, cycloheptyl, cyclobutene, cyclopentene, cyclohexene, cyclopentanediene, cyclohexadiene radicals, these cyclopropyl, cyclobutyl, cyclopentyl, cyclohexyl, cycloheptyl, cyclobutene, cyclopentene, cyclohexene, cyclopentanediene, cyclohexadiene radicals potentially being substituted themselves by one or more identical or different radicals chosen from among the halo, hydroxy, methyl, ethyl, propyl, isopropyl, butyl, isobutyl, sec-butyl, tert-butyl, pentyl, isopentyl, hexyl, isohexyl, vinyl, allyl, propenyl, butenyl, pentenyl, hexenyl, bromoethyl, trifluoromethyl, trifluoroethyl, pentafluoroethyl, methoxy, ethoxy, isopropyloxy, tert-butyloxy, methylthio, ethylthio, propylthio, butylthio, pentylthio, formyl, acetyl, propionyl, butyryl, pentanoyl, hexanoyl, acryloyl, crotonoyl, benzoyl, free or esterified carboxy, cyano, nitro, amino, methylamino, ethylamino, dimethylamino or diethylamino;

More particularly, the invention has as object the products described below in the examples, in particular the products complying to the following formulas:

- galanthaminium methanesulfonate;
- 10-N-demethyl-10-N-(4'-phthalimidobutyl)-galanthaminium trifluoroacetate;
- 10-N-demethyl-10-N-(6'-phthalimidohexyl)-galanthaminium trifluoroacetate;
- 10-N-demethyl-10-N-(8'-phthalimidooctyl)-galanthaminium bromohydrate;
- 10-N-demethyl-10-N-(10'-phthalimidodecyl)-galanthaminium bromohydrate;
- 10-N-demethyl-10-N-(12'-phthalimidododecyl)-galanthaminium bromohydrate;
- 10-N-demethyl-10-N-(6'-pyrrolohexyl)-galanthaminium bromohydrate;
- 6-O-demethyl-6-O-(4'-phthalimidobutyl)-galanthaminium bromohydrate;
- 6-O-demethyl-6-O-(8'-phthalimidooctyl)-galanthaminium bromohydrate;
- 6-O-demethyl-6-O-(10'-phthalimidodecyl)-galanthaminium bromohydrate;
- 6-O-demethyl-6-O-(12'-phthalimidododecyl)-galanthaminium bromohydrate;

The invention has as well as its object a preparation procedure for the products of general formula Ia and Ib such as defined above, characterized in that A) either the compound of general formula (1a) is oxidized directly,

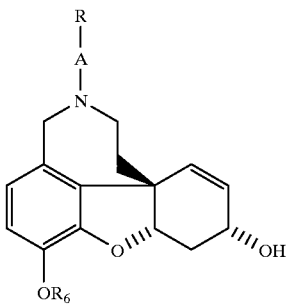

(Ia)

in which R, A and $R_6$ have the significance indicated above;

B) or the formula (1a) compound as defined above is converted to its N-oxide of formula (2a)

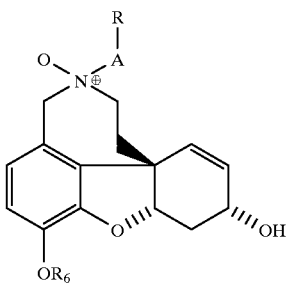

(2a)

in which R, A and $R_6$ have the significance indicated above, product of formula (2a) that is allowed to react with an acid anhydride in an inert atmosphere and inert solvent, at a temperature between 0° C. and ambient temperature, in order to obtain a formula Ia or Ib product in which $R_9$ represents a hydrogen atom, and if the formula Ia or Ib product in which $R_9$ represents $R'_9$ is sought, the product corresponding to formula Ia thus obtained in which $R_9$ represents a hydrogen atom is treated with a product representing a nucleophilic function of formula $R'_9Y$ in which $R'_9$ has the significance indicated above and Y represents a suitable radical, in order to obtain the formula (Ib) compound

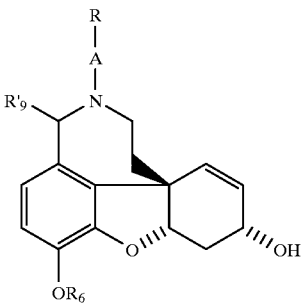

(Ib)

in which R, A, $R_6$ and $R'_9$ have the significance indicated above, subsequently A) either the general formula (1b) compound as defined above is oxidized directly, B) or the formula (1b) compound as defined above is converted to its N-oxide of formula (2b)

(2b)

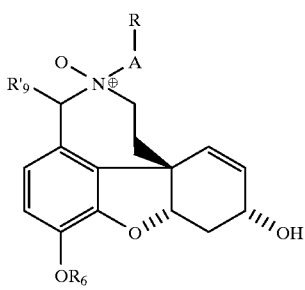

in which R, A, $R_6$ and $R'_9$ have the significance indicated above, product of formula (2b) that is reacted with an acid anhydride in an inert atmosphere and inert solvent at a temperature between 0° C. and ambient temperature,
in order to obtain a formula Ia or Ib product in which $R_9$ represents $R'_9$.

The products of the invention in which $R_9$ represents a hydrogen atom, may thus be obtained directly through the oxidation of compound (1a) or indirectly from that same formula (1a) compound. The products of the invention in which $R_9$ represents $R'_9$, may be obtained as well directly from the oxidation of the formula (1b) compound or indirectly from that same formula (1b) compound.

The direct oxidation may be conducted according to the methods of oxidation of amines, known by persons skilled in the art. In that manner, the oxidation may be conducted in an inert atmosphere, at a temperature between 10 and 30° C., in an aprotic solvent such as, for example, carbon tetrachloride in the presence of N-bromosuccinimide and azodiisobutyronitrile (AIBN). The oxidation may be carried out as well in the presence of iodine in a polar protic solvent such as, for example, ethanol.

The formula (1a) or (1b) compound is converted into its N-oxide corresponding to formula (2a) or (2b) respectively, according to one of the classic method of N-oxide preparation such as, for example, the reaction with a peracid under gentle conditions. The reaction of formula (2a) or (2b) compounds with an acid anhydride may be carried out in an inert solvent at a temperature between 0° C. and ambient temperature; it is preferably carried out with trifluoroacetic anhydride in dichloromethane.

Formula (1b) compound is obtained from a product corresponding to formula Ia in which $R_9$ represents a hydrogen atom, by allowing the latter to react with a product of formula $R'_9Y$ and representing a nucleophilic function, according to the classic methods of nucleophilic addition to imminium functions, methods known by persons skilled in the art; in this formula $R'_9Y$ product, $R'_9$ has the significance indicated above and Y may represent a metallic element as in the case of magnesium oxides, lithium oxides and alkyl-stannyles or Y represents respectively MgHalogen, Li, $Sn(Y')_3$ in which Y' represents an alkyl radical with 1 to 6 carbon atoms, and preferably the methyl, butyl or allyl radical.

Formula (1) compounds in which R represents a hydrogen atom, are described in European Patent EP 236684.

The formula (1a) compounds in which R represents a —NR'R" or —N⊕R'R"R" may be obtained from galanthamine according to the reaction diagram 1 below. The O-demethylation reactions, addition of a formula R—A—X compound in which R and A are such as defined above and X represents a halogen atom, or oxidation such as defined in the reaction diagram 1, are implemented according to the classic methods known by persons skilled in the art. Moreover, the formula (1a) compound in which R represents a phthalimido group, may be used as a starting compound for the synthesis of a formula (1a) compound in which —NR'R" represents —$NH_2$. Said (1a) compound in which —NR'R" represents —$NH_2$ may itself be used as well as starting compound for the synthesis of compounds (I) in which —NR'R" represents a substituted amino group.

The invention has as well as its object, as novel industrial products, and notably as novel industrial products intended for the preparation of formula Ia or Ib products, the products of formula (1a), (1b), (2a) and (2b) such as described above, in which R represents a group of formula —NR'R" or —N⊕R'R"R" such as defined above.

Reaction Diagram I

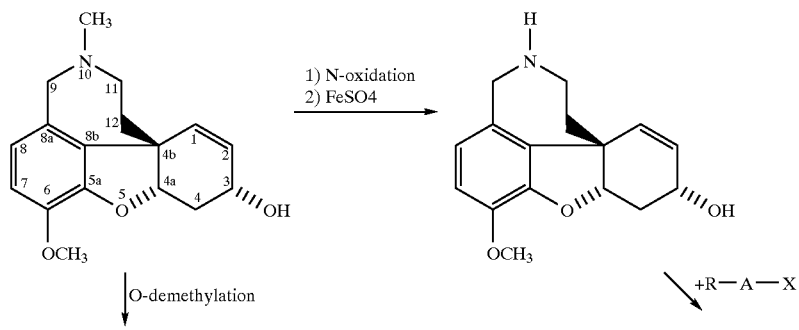

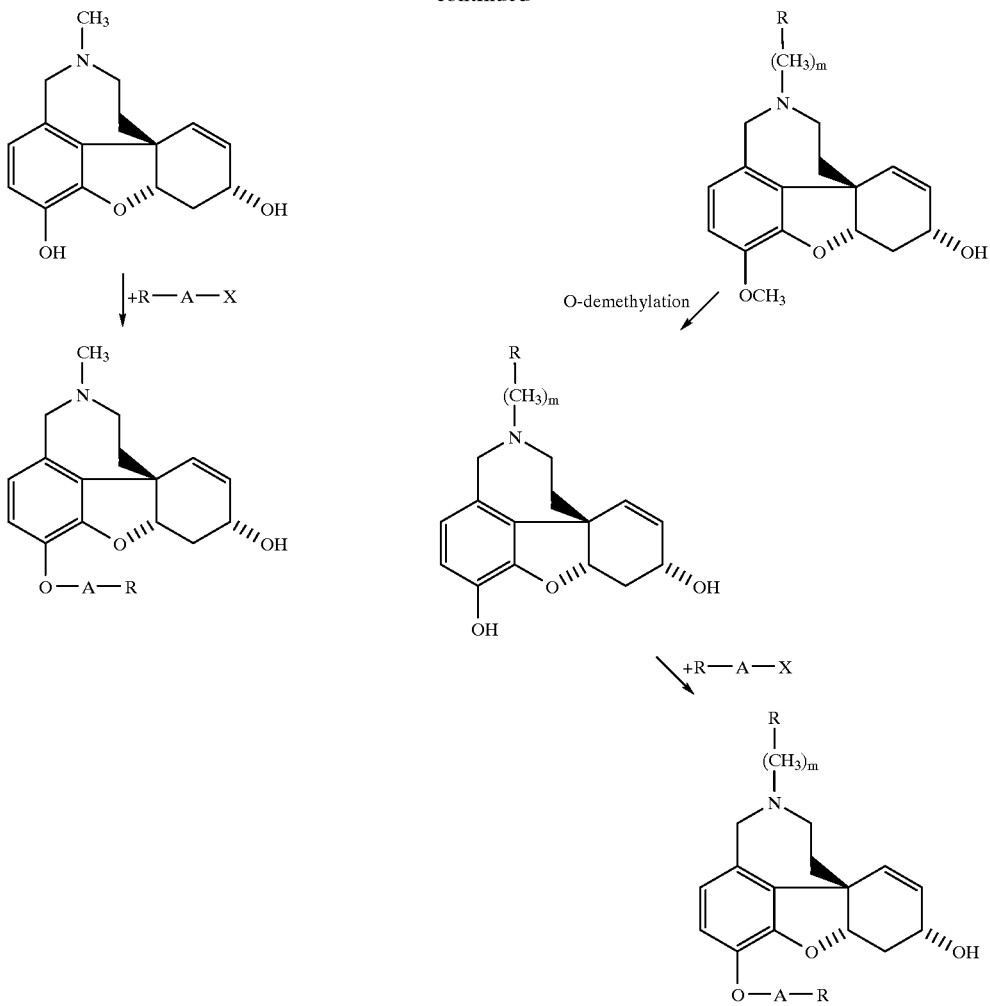

The compounds of the present invention are cholinesterase inhibitors. This property makes them suitable for pharmaceutical use. They may thus be used in different therapeutic applications. Hence, the compounds of the invention may be used for the treatment of neurodegencrative illnesses as well as Alzheimer type senile dementias.

In the experimental section below, an illustration can be found of the pharmacological properties of these compounds of the invention.

The present application has as well as object, as medications, formula Ia and Ib products such as defined above, as well as the addition salts of the pharmaceutically acceptable mineral or organic acids of said formula Ib products, as well as the pharmaceutical compositions comprising, as an active ingredient, at least one of the medications as defined above.

The invention concerns thus the pharmaceutical compositions comprising as an active ingredient, at least one of the medications as defined above, in association with a pharmaceutically acceptable medium. The pharmaceutical composition may be in the form of solids, for example, powders, granules, tablets, capsules, or suppositories. The appropriate solid mediums may be, for example, calcium phosphate, magnesium stearate, talc, sugars, lactose, dextrine, amidon, gelatin, cellulose, methyl cellulose, sodium carboxymethyl cellulose, polyvinylpyrrolidine and wax.

The pharmaceutical compositions comprising a compound of the invention may also be present in the form of a liquid, for example, as solutions, emulsions, suspensions or syrups. The appropriate liquid mediums may be for example, water, organic solvents such as glycerol or glycols.

The compositions according to the invention may be administered by classic methods of administration such as oral, parenteral or intramuscular.

The invention has as well as its object the use of formula Ia (or Ib) products, such as defined above, for the preparation of medications intended to treat neurodegenerative diseases as well as medications intended for the treatment senile dementias.

The following examples are presented in order to illustrate the above procedures and should not be considered as limiting in any way the scope of the invention.

EXPERIMENTAL SECTION

Preparation 1 norgalanthamine

A solution of 1.73 g (5.7 mmoles) of galanthamine N-oxide and 3.17 g (11,4 mmoles, 2 eq) of $FeSO_4$—$7H_2O$ in 100 ml of methanol is agitated under argon for 1.5 hours at 10° C. After the evaporation of the solvent, the residue is taken up again in dichloromethane, treated with a saturated aqueous solution of sodium hydrogencarbonate and extracted three times with dichloromethane. The organic phases are collected and washed with a saturated aqueous solution of sodium chloride, dried on sodium sulfate and evaporated. The crude product of the reaction is purified by flash chromatography on silica gel using the mixture of dichloromethane/methanol (80:20) as eluant. The least polar fraction yields galanthamine and the most polar fraction yields for the most part norgalanthamine in the form of a white foam (yield=76%).

NMR- $^1$H (300 MHz-CD$_3$OD): 6.71 (1H, d, J=8 Hz, H$_7$); 6.63 (1H, d, J=8 Hz, H$_8$); 6.12 (1H, d, J=10 Hz, H$_1$); 5.91 (1H, dd, J$_1$=10 Hz, J$_2$=5 Hz, H$_2$); 4.53 (1H, s large, H$_{4a}$); 4.14 (1H, t large, J=5 Hz, H$_3$); 4.06 (1H, d J=15 Hz, H$_{9\alpha}$); 3.89 (1H, d, J=15 Hz, H$_{9\beta}$); 3.79 (3H, s, OCH$_3$); 3.25 (2H, m, H$_{11}$); 2.49 (1H, dm, J=16 Hz, H$_{4\alpha}$); 2.24 (1H, ddd, J$_1$=16 Hz, J$_2$=5 Hz, J$_3$=3 Hz, H$_{4\beta}$); 1.84 (2H, m, H$_{12}$.

Preparation 2

10-N-demethyl-10-N-(4'-phthalimidobutyl)-galanthamine 2.11 g (7.5 mmoles, 1.2 eq) of N-(4-bromobutyl) phthalimide and 1.7 ml of triethylamine is added to a solution of 1.70 g (6.2 mmoles) of norgalanthamine in 50 ml of acetonitrile. The reaction mixture is agitated and subsequently brought to reflux for 20 hours. After the evaporation of the solvent, the residue is taken up again in 10 ml of dichloromethane and 10 ml of water. A 1N hydrochloric acid solution is added until a pH of 4–5 is attained. The organic phase is recovered, washed three times with a saturated aqueous solution of sodium carbonate, dried on sodium sulfate, filtered and evaporated. The crude product is purified by chromatography on silica gel with a mixture of dichloromethane/methanol (90:10) as cluant yielding the final product in the form of a yellow oil. (yield=81%).

NMR- $^1$H (300 MHz-CD$_3$OD): 7.83–7.72 (4H, m, phthalimido); 6.61 (1H, d, H$_7$); 6.54 (1H, d, H$_8$); 6.14 (1H, d, H$_1$); 5.91 (1H, dd, H$_2$); 4.53 (1H, large, s, H$_{4a}$); 4.15 (1H, d, H$_{9\alpha}$); 4.13 (1H, large, t, H$_3$); 3.77(1H, d, H$_{9\beta}$); 3.75 (3H, s, OCH$_3$); 3.65 (2H, t, H$_{4'}$); 3.34 (1H, large t, H$_{11\alpha}$); 3.14 (1H, dm, H$_{11\beta}$); 2.57–2.44 (3H, m, H$_{1'}$, H$_{4\alpha}$); 2.14–2.01 (2H, m, H$_{12\alpha}$, H$_{4\beta}$); 1.63 (2H, m, H$_{2'}$); 1.59–1.48 (3H, m, H$_{3'}$, H$_{12\beta}$).

Preparation 3

10-N-demethyl-N-(6'-phthalimidohexyl)-galanthamine

The reaction is conducted according to the method described in the example of preparation 2 using N-(6-bromohexyl)-phthalimide in place of N-(4-bromobutyl)-phthalimide (yield=80%).

NMR- $^1$H (300 MHz-CDCl$_3$): 7.85–7.82 (2H, m, phthalimido); 7.72–7.69 (2H, m, phthalimido); 6.66 (1H, d, H$_7$); 6.61 (1H, d, H$_8$); 6.09 (1H, d, H$_1$); 6.00 (1H, dd, H$_2$); 4.61 (1H, large s, H$_{4a}$); 4.14 (1H, large t, H$_3$); 4.12 (1H, d, H$_{9\alpha}$); 3.83 (3H, s, OCH$_3$); 3.80 (1H, d, H$_{9\beta}$); 3.66 (2H, t, H$_{6'}$); 3.35 (1H, large t, H$_{11\alpha}$); 3.16 (1H, large d, H$_{11\beta}$) 2.68 (1H, dm, H$_{4\beta}$); 2.52–2.39 (2H, m, H$_{1'}$); 2.10–1.96 (2H, m, H$_{12\alpha}$, H$_{4\beta}$); 1.72–1.60 (2H, m, H$_{5'}$); 1.54–1.41(3H, m, H$_{2'}$, H$_{12\beta}$); 1.38–1.29(4H, m, H$_{4'}$, H$_{3'}$).

Preparation 4

10-N-demethyl-10-N-(4'-phthalimidobutyl)-galanthamine N-oxide 116 mg (0.67 mmol, 1.1 eq) of 70% metachloroperbenzoic acid is added to a solution of 203 mg (0.43 mmole) of 10-N-demethyl-10-N-(4'-phthalimidobutyl)-galanthamine in 10 ml of dichloromethane anhydride. The reaction mixture is agitated for two and one half hours in an inert atmosphere at ambient temperature. The solvent is evaporated in vacuum and the residue is purified by flash chromatography on silica gel using a mixture of dichloromethane/methanol (80:20) as eluant to yield the pure product in the form of a white foam (86%).

NMR- $^1$H (250 MHz-CD$_3$OD): 7.82–7.70 (4H, m, phthalimido); 6.80–6.55 (2H, s, H$_7$, H$_8$); 6.08 (2H, s, H$_1$, H$_2$); 4.84 (1H, large d, H$_{9\alpha}$); 4.69 (1H, large s, H$_{4a}$); 4.41 (1H, d, H$_{9\beta}$); 4.18 (1H, t, H$_3$); 4.11–3.89 (1H, m, H$_{11\alpha}$); 3.85–3.78 (1H, m, H$_{11\beta}$); 3.82 (3H, s, OCH$_3$); 3.64 (2H, t, H$_{4'}$); 3.15–3.05 (2H, m, H$_{1'}$); 2.71 (1H, dm, H$_{4\alpha}$); 2.05 (1H, ddd, H$_{4\beta}$); 1.97–1.83 (2H, m, H$_{12}$); 1.75–1.63 (4H, m, H$_{2'}$, H$_{3'}$).

Preparation 5

10-N-demethyl-10-N-(8'-phthalimidooctyl)-galanthamine

The reaction is conducted according to the method described in the example of phthalimide (yield 82%).

NMR- $^1$H (300 MHz-CDCl$_3$): 7.84 (2H, m, H$_{ar\,meta}$); 7.71 (2H, m, H$_{ar\,ortho}$); 6.66 (1H, d, J=8 Hz, H$_7$); 6.61 (1H, d, J=8 Hz, H$_8$); 6.08 (1H, d, J=10 Hz, H$_1$); 6.00 (1H, dd, J$_1$=10 Hz, J$_2$=4.5 Hz, H$_2$); 4.61 (1H, large s, H$_{4a}$); 4.14 (1H, large t, H$_3$); 4.13 (1H, d, J=15 Hz, H$_{9\alpha}$); 3.83 (3H, s, OCH$_3$); 3.80 (1H, d, J=15 Hz, H$_{9\beta}$); 3.66 (2H, t, J=7 Hz, H$_{8'}$); 3.35 (1H, large t, J$_1$=15 Hz, J$_2$=13 Hz, H$_{11\alpha}$); 3.17 (1H, large d, J=15 Hz, H$_{11\beta}$); 2.68 (1H, dm, J=15.5 Hz, H$_{4\alpha}$); 2.46 (2H, m, H$_{1'}$); 2.40 (1H, large s, OH); 2.08–1.97 (2H,m, H$_{12\alpha}$, H$_{4\beta}$); 1.65 (2H, m, H$_{7'}$); 1.54–1.43 (3H, m, H$_{12\beta}$, H$_{2'}$); 1.31 (4H, large s, H$_{6'}$, H$_{3'}$); 1.26 (4H, m, H$_{4'}$, H$_{5'}$).

Preparation 6

10-N-demethyl-10-N-(10'-phthalimidodecyl)-galanthamine

The reaction is conducted according to the method described in the example of preparation 2 using N-(10-bromodecyl)-phthalimide in place of N-(4-bromobutyl)-phthalimide (yield 84%).

NMR- $^1$H (300 MHz-CDCl$_3$): 7.82 (2H, m, H$_{ar\,meta}$); 7.70 (2H, m, H$_{ar\,ortho}$); 6.66 (1H, d, J=8 Hz, H$_7$); 6.61 (1H, d, J=8 Hz, H$_8$); 6.09 (1H, d, J=10 Hz, H$_1$); 5.99 (1H, dd, J$_1$=10 Hz, J$_2$=5 Hz, H$_2$); 4.61 (1H, large s, H$_{4a}$); 4.14 (1H, large t, H$_3$); 4.13 (1H, d, J=15 Hz, H$_{9\alpha}$); 3.82 (3H, s, OCH$_3$); 3.81 (1H, d, J=15 Hz, H$_{9\beta}$); 3.66 (2H, t, J=7 Hz, H$_{10'}$); 3.35 (1H, large t, J$_1$=15 Hz, J$_2$=13 Hz, H$_{11\alpha}$); 3.17 (1H, large d, J=15 Hz, H$_{11\beta}$); 2.67 (1H, dm, J=14 Hz, H$_{4\alpha}$); 2.47 (2H, m, H$_{1'}$); 2.09–1.97 (2H, m, H$_{12\alpha}$, H$_{4\beta}$); 1.66 (2H, m, H$_{9'}$); 1.54–1.46 (3H, m, H$_{12\beta}$, H$_{2'}$); 1.31 (2H, large s, H$_{8'}$); 1.25 (10H, large s, H$_{3'}$, H$_{4'}$, H$_{5'}$, H$_{6'}$, H$_{7'}$).

Preparation 7

10-N-demethyl-10-N-(12'-phthalimidododecyl)-galanthamine

The reaction is conducted according to the method described in the example of preparation 2 using N-(12-bromododecyl)-phthalimide in place of N-(4-bromobutyl)-phthalimide (yield 81%).

NMR- $^1$H (300 MHz-CDCl$_3$): 7.84 (2H, m, H$_{ar\,meta}$); 7.70 (2H, m, H$_{ar\,ortho}$); 6.66 (1H, d, J=8 Hz, H$_7$); 6.61 (1H, d, J=8

Hz, $H_8$); 6.09 (1H, d, J=10 Hz, $H_1$); 6.00 (1H, dd, $J_1$=10 Hz, $J_2$=5 Hz, $H_2$); 4.61 (1H, large s, $H_{4a}$); 4.14 (1H, large t, $H_3$); 4.13 (1H, d, J=15 Hz, $H_{9\alpha}$); 3.83 (3H, s, $OCH_3$); 3.82 (1H, d, J=15 Hz, $H_{9\beta}$); 3.67 (2H, t, J=7 Hz, $H_{12'}$); 3.36 (1H, large t, $J_1$=15 Hz, $J_2$=13 Hz, $H_{11\alpha}$); 3.18 (1H, large d, J=15 Hz, $H_{11\beta}$); 2.68 (1H, dm, J=15.5 Hz, $H_{4\alpha}$); 2.46 (3H, m, OH, $H_{1'}$); 2.05–1.96 (2H, m, $H_{12\alpha}$,—$H_{4\beta}$); 1.66 (2H, m, $H_{11'}$); 1.54–1.45 (3H, m, $H_{12\beta}$,—$H_{2'}$); 1.31 (2H, m, $H_{10'}$); 1.24 (14H, large s, $H_{3'}$, $H_{4'}$, $H_{5'}$, $H_{6'}$,—$H_{7'}$, $H_{8'}$, $H_{9'}$).

Preparation 8

6-O-demethylgalanthamine 8 ml (7.96 mmoles, 4.5 eq) of 1M L-selectride in tetrahydrofuran is added to a solution of 507 mg (1.77 mmoles) of galanthamine in 20 ml of tetrahydrofuran. The mixture is heated under argon at 67° C. for 20 hours. The reaction mixture is chilled to 0° C., diluted with 25 ml of ethyl acetate, subsequently 25 ml water is added slowly. The aqueous phase is separated from the organic phase and concentrated in vacuum. The crude product is purified by flash chromatography on silica gel with a mixture of dichloromethane/methanol/ammonia (90:9:1) in order to obtain a beige solid, which, after recrystalization in acetone yields the 6-O-demethylgalanthamine (yield=95%).

NMR- $^1$H (250 MHz-$CD_3OD$): 8.06 (H, s, $H_9$); 7.24 (1H, d, J=8.5 Hz, $H_8$); 6.43(1H, d, J=8.5 Hz, $H_7$); 6.01 (1H, dd, $J_1$=10 Hz, $J_2$=5 Hz, $H_2$); 5.78 (1H, d, J=8.5 Hz, $H_1$); 4.53 (1H, large s, $H_{4a}$); 4.15–4.05 (2H, m, $H_3$, $H_{11\alpha}$); 3.81 (1H, dm, J=16 Hz, $H_{11\beta}$); 3.57 (3H, s, $NCH_3$); 2.56 (1H, dm, J=15.5 Hz, $H_{4\alpha}$); 2.18–2.06 (3H, m, $H_{4\beta}$, $H_{12}$).

Preparation 9

6-O-demethyl-6-O-(4'-phthalimidobutyl)-galanthamine

A solution of 79 mg (0.29 mmole) of 6-O-demethylgalanthamine and 94 mg (0.29 mmole) of cesium carbonate in 3 ml of distilled dimethylformamide is agitated at ambient temperature for 30 minutes. 90 mg (0.32 mmole, 1.1 eq) of N-(4-bromobutyl)-phthalimide are then added and the mixture is heated at reflux for 2 hours. After evaporation of the solvent in vacuum, the residue is taken up again in 3×20 ml of dichloromethane and washed with 50 ml of a saturated aqueous solution of sodium chloride. The organic phases are recombined, dried over sodium sulfate, filtered and evaporated. The crude product is purified by thick bed chromatography using as an elution mixture: dichloromethane 90/methanol 10/ammonia vapors (yield=70%).

NMR- $^1$H (300 MHz-$CDCl_3$): 7.89 (2H, m, $H_{ar\ ortho}$); 7.77 (2H, m, $H_{ar\ meta}$); 6.64 (1H, d, J=8 Hz, $H_7$); 6.58 (1H, d, J=8 Hz, $H_8$); 6.05 (1H, d, J=10 Hz, $H_1$); 6.02 (1H, dd, $J_1$=10 Hz, $J_2$=4.5 Hz, $H_2$); 4.57 (1H, large s, $H_{4a}$); 4.11 (1H, large t, J=4.5 Hz $H_3$); 4.10 (1H, d, J=15 Hz, $H_{9\alpha}$); 3.95 (2H, m, $H_4$); 3.69 (1H, d, J=15 Hz, $H_{9\beta}$); 3.68 (2H, t, J=7 Hz, $H_{1'}$); 3.28 (1H, large t, $J_1$=14 Hz, $H_{11\alpha}$); 3.06 (1H, large d, J=14 Hz, $H_{11\beta}$); 2.68 (1H, dm, J=16 Hz, $H_{4\alpha}$); 2.42 (3H, s, $NCH_3$); 2.11 (1H, dm, J=15 Hz, $H_{12\alpha}$); 1.99 (1H, ddd, J=15 Hz, $H_{4\beta}$); 1.89–1.72 (3H, m, $H_{2'}$, $H_{12\beta}$); 1.63 (2H, m, $H_{3'}$).

Preparation 10

6-O-demethyl-6-O-(8'-phthalimidooctyl)-galanthamine

Working in the same manner as in the case of preparation 9 but using N-(8-bromooctyl)phthalimide in place of N-(4-bromobutyl)phthalimide, the sought compound is obtained (yield 45%).

NMR- $^1$H (200 MHz-$CDCl_3$):7.83 (2H, m, $h_{ar\ ortho}$); 7.71 (2H, m, $H_{ar\ meta}$); 6.65 (1H, d, J=8 Hz, $H_7$); 6.58 (1H, d, J=8 Hz, $H_8$); 6.05 (1H, d, J=10.25 Hz, $H_1$); 5.98 (1H, dd, $J_1$=10.25 Hz, $J_2$=4.5 Hz, $H_2$); 4.59 (1H, large s, $H_{4a}$); 4.12 (1H, large t, $H_3$); 4.08 (1H, d, J=15 Hz, $H_{9\alpha}$); 4.02 (2H, m, $H_{8'}$); 3.67 (1H, d, J=16 Hz, $H_{9\beta}$); 3.66 (2H, t, J=6.5 Hz, $H_{1'}$); 3.28 (1H, large t, $J_1$=14 Hz, $J_2$=13 Hz, $H_{11\alpha}$); 3.04 (1H, m, J=14 Hz, $H_{11\beta}$); 2.83 (1H, large s, OH); 2.68 (1H, dm, J=16 Hz, $H_{4\alpha}$); 2.39 (3H, s, $NCH_3$); 2.11 (1H, dm, J=13.5 Hz, $H_{12\alpha}$); 1.99 (1H, ddd, J=16 Hz, $H_{4\beta}$); 1.75–1.53 (5H, m, $H_{7'}$, $H_{2'}$, $H_{12\beta}$,); 1.33 (8H, large s, $H_{3'}$, $H_{6'}$,—$H_{4'}$, $H_{5'}$).

Preparation 11

6-O-demethyl-6-O-(10'-phthalimidodecyl)-galanthamine

Working in the same manner as in the case of preparation 9 but using N-(10-bromodecyl)phthalimide in place of N-(4-bromobutyl)phthalimide, the sought compound is obtained (yield 48%).

NMR- $^1$H (300 MHz-$CDCl_3$): 7.84 (2H, m, $H_{ar\ meta}$); 7.71 (2H, m, $H_{ar\ ortho}$); 6.65 (1H, d, J=8 Hz, $H_7$); 6.60 (1H, d, J=8 Hz, $H_8$); 6.05 (1H, d, J=10 Hz, $H_1$); 6.00 (1H, dd, $J_1$=10.25 Hz, $J_2$=5 Hz, $H_2$); 4.58 (1H, large s, $H_{4a}$); 4.13 (1H, large t, $H_3$); 4.12 (1H, d, J=15.5 Hz, $H_{9\alpha}$); 4.01 (2H, t, J=6.5 Hz, $H_{10'}$); 3.67 (1H, d, J=15.5 Hz, $H_{9\beta}$); 3.65 (2H, t, J=7 Hz, $H_{1'}$); 3.27 (1H, large t, $J_1$=14.5 Hz, $J_2$=13 Hz, $H_{11\alpha}$); 3.16 (1H, large d, J=14.5 Hz, $H_{11\beta}$); 2.66 (1H, dm, J=16 Hz, $H_{4\alpha}$); 2.44 (1H, s, OH); 2.36 (3H, s, $NCH_3$); 2.07 (1H, dm, J=13 Hz, $H_{12\alpha}$); 1.99 (1H, dm, J=16 Hz, $H_{4\beta}$); 1.74–1.53 (5H, m, $H_{2'}$, $H_{9'}$, $H_{12\beta}$,); 1.31 (12H, large s, $H_{3'}$, $H_{4'}$, $H_{5'}$, $H_{6'}$, $H_{7'}$, $H_{8'}$).

Preparation 12

6-O-demethyl-6-O-(12'-phthalimidododecyl)-galanthamine

Working in the same manner as in the case of preparation 9 but using N-(12-bromododecyl)phthalimide in place of N-(4-bromobutyl)phthalimide, the sought compound is obtained (yield 67%).

NMR- $^1$H (300 MHz-$CDCl_3$): 7.85 (2H, m, $H_{ar\ meta}$); 7.70 (2H, m, $H_{ar\ ortho}$); 6.66 (1H, d, J=8 Hz, $H_7$); 6.59 (1H, d, J=8 Hz, $H_8$); 6.07 (1H, d, J=10 Hz, $H_1$); 5.99 (1H, dd, $J_1$=10 Hz, $J_2$=4.5 Hz, $H_2$); 4.60 (1H, large s, $H_{4a}$); 4.14 (1H, large t, $H_3$); 4.13 (1H, d, J=15 Hz, $H_{9\alpha}$); 4.03 (2H, t, J=7 Hz, $H_{12'}$); 3.69 (1H, d, J=15 Hz, $H_{9\beta}$); 3.66 (2H, t, J=7 Hz, $H_{1'}$); 3.29 (1H, large t, $J_1$=15 Hz, $J_2$=13 Hz, $H_{11\alpha}$); 3.18 (1H, large d, J=15 Hz, $H_{11\beta}$); 2.67 (1H, dm, J=16 Hz, $H_{4\alpha}$); 2.46 (1H, s, OH); 2.38 (3H, s, $NCH_3$); 2.09 (2H, 1H, dm, J=14 Hz, $H_{12\alpha}$); 1.96 (1H, dm, J=16 Hz, $H_{4\beta}$); 1.76–1.55 (5H, m, $H_{2'}$, $H_{11'}$, $H_{12\beta}$); 1.35 (16H, large s, $H_{3'}$, $H_{4'}$, $H_{5'}$, $H_{6'}$,—$H_{7'}$, $H_{8'}$, $H_{9'}$, $H_{10'}$).

Preparation 13

10-N-demethyl-10-N-(6'-aminohexyl)-galanthamine

To a solution of 1.67 g (3.32 mmoles) of 10-N-demethyl-10-N-(6'-phthalimidohexyl)-galanthamine in 50 ml of ethanol at 95° C. are added drop wise 323 μl (2 eq, 6.64 mmoles) of hydrated hydrazine. The mixture is agitated and brought to reflux for 18 hours. A 5N solution of hydrochloric acid is added until a pH of 1 is attained. The white precipitate formed is removed by filtration and the filtrate is subsequently concentrated. The residue is then dissolved in 60 ml of ethanol/water (2:1) and sodium carbonate is added until a pH of 10 is attained. The solution is extracted with 5×50 ml of dichloromethane. The organic phase is dried over sodium sulfate, filtered and evaporated. The residue is purified by flash chromatography with a mixture of dichloromethane/methanol/ammonia (88:10:2) resulting in a white solid (yield 75%).

NMR- $^1$H (300 MHz-CDCl$_3$): 6.66 (1H, d, J=8.25 Hz, H$_7$); 6.61 (1H, d, J=8.25 Hz, 6.09 (1H, d, J=10.25 Hz, H$_1$); 5.99 (1H, dd, J$_1$=10.25 Hz, J$_2$=4.75 Hz, H$_2$); 4.61 (1H, s large, H$_{4a}$); 4.14 (1H, t large, J=4.75 Hz, H$_3$); 4.13 (1H, d, J=15.5 Hz, H$_{9\alpha}$); 3.83 (3H, s, OCH$_3$); 3.81 (1H, d, J=15.5 Hz, H$_{11\beta}$); 3.35 (1H, large t, J=13 Hz, H$_{11\alpha}$); 3.17 (1H, large d, J=15 Hz, H$_{11\beta}$); 2.68 (1H, dm, J=16 Hz, H$_{4\alpha}$); 2.66 (2H, t, J=7 Hz, H$_6$); 2.55–2.40 (2H, m, H$_{1'}$); 2.09–2.04 (2H, m, H$_{12\alpha}$); 2.01 (1H, m, H$_{12\alpha}$); 2.01 (1H, ddd, J$_1$=16 Hz, J$_2$ =5 Hz, H$_{4\beta}$); 1.77 (1H, large s, NH$_2$, OH); 1.55–1.37 (5H, m, H$_{12\beta}$, H$_{2'}$, H$_{5'}$); 1.35 –1.23 (4H, m, H$_{4'}$, H$_{3'}$).

Preparation 14

10-N-demethyl-10-N-(6'pyrrolohexyl)-galanthamine 198 mg (2.40 mmoles, 2 eq) of sodium acetate are added to a solution of 75 mg (0.20 mmole) of 10-N-demethyl-10-N-(6'-aminohexyl)-galanthamine in 1.5 ml of acetic acid (pH reaction=7). The mixture is heated at 70° C. under argon for 10 minutes then 29 µl (0.22 mmole, 1.1 eq) of 2,5-dimethoxy-tetrahydrofuran is added. At the end of 3 hours, 10 ml of water is added (pH 5) and subsequently small quantities of sodium carbonate to return the solution to pH 9. The aqueous phase is then extracted with 3×30 ml ethyl acetate. The organic phase is dried over sodium sulfate, filtered and evaporated. The residue is separated by thick bed chromatography with a mixture of dichloromethane/methanol/ammonia (90:10:vapors) resulting in the compound in the form of a colorless oil (yield 79%).

NMR- $^1$H (250 MHz-CDCl$_3$): 6.67 (1H, d, J=8.25 Hz, H$_7$); 6.64 (2H, t, J=2 Hz, H$_{8'}$, H$_{11'}$); 6.61(1H, d, J=8.25 Hz, H$_8$); 6.14 (2H, t, J=2 Hz, H$_{9'}$, H$_{10'}$); 6.09 (1H, dd, J$_1$=10.5 Hz, J$_2$=1 Hz, H$_1$); 6.00 (1H, dd, J$_1$=10.5 Hz, J$_2$=4.5 Hz, H$_2$); 4.61 (1H, s large, H$_{4a}$); 4.15 (1H, t large, J=4.75 Hz, H$_3$); 4.14 (1H, d, J=15.5 Hz, H$_{9\alpha}$); 3.86 (2H, t, J=7 Hz, H$_6$); 3.84 (3H, s, OCH$_3$); 3.81 (1H, d, J=15.5 Hz, H$_{9\beta}$); 3.37 (1H, large t, J$_1$=15 Hz, J$_2$=13 Hz H$_{11\alpha}$); 3.16 (1H, dt, J$_1$=15 Hz, J$_2$=5, J$_3$=3H$_{11\beta}$); 2.73–2.65 (2H, m, H$_{4\beta}$, OH); 2.56–2.38 (2H, m, H$_{1'}$); 2.10–2.05 (1H, m, H$_{12\alpha}$); 2.01 (1H, ddd, J$_1$=16 Hz, J$_2$=5.5 Hz, J$_3$=2.5 Hz, H$_{4\beta}$); 1.75 (2H, m, H$_{5'}$); 1.55–1.42 (3H, m, H$_{12\beta}$, H$_{2'}$); 1.32–1.27 (4H, m, H$_{4'}$, H$_{3'}$).

EXAMPLE 1 galanthaminium methanesulfonate 87 mg (0.49 mmole, 1.3 eq) of N-bromosuccinimide is added to a solution of 127 mg (0.44 mmole) of galanthamide in 5 ml of carbon tetrachloride. The reaction mixture is agitated for 21 hours at ambient temperature in an inert atmosphere. Extraction with dichloromethane (3×30 ml) and a saturated aqueous solution of sodium carbonate is carried out. The organic phase is dried on sodium sulfate, filtered and evaporated in vacuum. The crude product thus obtained is taken up again with 5 ml of tetrahydrofuran and 76 µl of methansulfonic acid. The mixture is agitated at ambient temperature in an inert atmosphere for one hour. After evaporation of the solvent, the crude product is washed with ethyl acetate, then purified on a preparative plaque with a mixture of dichloromethane/methanol (80/20) as eluant in order to obtain the sought compound in its methanesulfonate form (yield=64%).

NMR- $^1$H (250 MHz-CDCl$_3$): 8.67 (1H, s, H$_9$); 7.51 (1H, d, H$_7$); 7.05 (1H, d, H$_8$); 6.21 (1H, dd, H$_2$); 5.71 (1H, d, H$_1$); 4.87 (1H, large s, H$_{4a}$); 4.54 (1H, dd, H$_3$); 4.30–4.10 (2H, m, H$_{11}$); 4.02 (3H, s, NCH$_3$); 3.88 (3H, s, OCH$_3$); 2.85 (1H, m, H$_{4\alpha}$); 2.30–2.10 (3H, m, H$_{4\beta}$, H$_{12}$).

EXAMPLE 2

10-N-demethyl-10-N-(4'-phthalimidobutyl)-galanthaminium trifluoroacetate

308 µl (2.2 mmole, 6 eq) trifluoroacetic anhydride freshly distilled to a solution at 0° C. of 178 mg (0.36 mmole) of 10-N-demethyl-10-N-(4'-phthalimidobutyl)-galanthamine in 10 ml of dichloromethane. The reaction mixture is agitated for 3 hours at 0° C. under argon and subsequently allowed to warm up to ambient temperature. The solvent is evaporated in vacuum, the crude product is subsequently purified by thick bed chromatography with a mixture of methanol/dichloromethane/ammonia (5/95/vapors) as eluant in order to obtain 79 mg of compound Ib: 10-N-demethyl-10-N-(4'-phthalimidobutyl)-9-hydroxy-galanthamine. After purification, said compound Ib is converted to the corresponding Ia compound in the presence of trifluoroacetic acid (yield=44%).

NMR- $^1$H (300 MHz-CDCl$_3$): 8.77 (1H, s, H$_9$); 7.85–7.72 (4H, m, phthalimido); 7.59 (1H, d, H$_8$); 7.02 (1H, d, H$_7$); 6.14 (1H, dd, H$_2$); 5.62 (1H, d, H$_1$); 4.81 (1H, large s, H$_{4a}$); 4.38 (1H, large t, H$_3$); 4.27–4.05 (2H, m, H$_{11}$); 3.98 (3H, s, OCH$_3$); 3.77 (2H, large t, H$_{4'}$); 2.78 (1H, dm, H$_{4\alpha}$); 2.26 (2H, large t, H$_{1'}$); 2.22 (1H, m, H$_{4\beta}$); 2.13 (1H, ddd, H$_{12\alpha}$); 2.00 (2H, m, H$_{2'}$); 1.88–1.66 (3H, m, H$_{3'}$, H$_{12\beta}$).

EXAMPLE 3

10-N-demethyl-10-N-(6'-phthalimidohexyl)-galanthaminium trifluoroacetate

The reaction is conducted according to the method described in example 2 but using 10-N-demethyl-10-N-(6'-phthalimidohexyl)-galanthamine N-oxide in place of 10-N-demethyl-10-N-(4'-phthalimidobutyl)-galanthamine N-oxide (yield 58%).

NMR- $^1$H (300 MHz-CDCl$_3$): 8.95 (1H, s, H$_9$); 7.88–7.78 (4H, m, phthalimido), 7.69 (1H, d, H$_8$); 7.02 (1H, d, H$_7$); 6.15 (1H, dd, $_2$); 5.60 (1H, d, H$_1$); 4.78 (1H, large s, H$_{4a}$); 4.25 (1H, large t, H$_3$); 4.19–4.02 (2H, m, H$_{11}$); 3.98 (3H, s, OCH$_3$); 3.66 (2H, t, $_{6'}$); 2.77 (1H, dm, H$_{4\alpha}$); 2.25 (2H, m, H$_{1'}$); 2.12 (1H, dm, H$_{4\beta}$); 2.00–1.88 (2H, m, H$_{5'}$); 1.78–1.63 (3H, m, ,H$_{12\alpha}$, H$_{2'}$); 1.52–1.35 (5H, m, H$_{3'}$, H$_{4'}$, H$_{12\beta}$).

EXAMPLE 4

10-N-demethyl-10-N-(8'-phthalimidooctyl)-galanthaminium bromohydrate

EXAMPLE 4a

Indirect Synthesis

The reaction is conducted according to the method described in example 2 but using 10-N-demethyl-10-N-(8'-phthalimidooctyl)-galanthamine N-oxide in place of 10-N-demethyl-10-N-(4'-phthalimidobutyl)-galanthamine N-oxide.

EXAMPLE 4b

Direct Systhesis 32 mg (0.18 mmole, 1.3 eq) of N-bromosuccinimide and a catalytic quantity of azodiisobutyronitrile (5%) is added to a solution of 72 mg (0.14 mmole) of 10-N-demethyl-10-N-(8'-phthalimidooctyl)-galanthamine in 2 ml of carbon tetrachloride. The mixture is agitated at ambient temperature under argon and shaded from light for 24 hours. Then 40 ml of dichloromethane is added and the mixture is washed with 20 ml of a saturated aqueous solution of sodium chloride, filtered and evaporated in vacuum. The residue is purified by thick bed chromatography with an eluant mixture of dichloromethane 90/methanol 9.9 /hydrobromic acid 0.5% 0.1 (yield=52%).

NMR- $^1$H (300 MHz-CDCl$_3$): 10.09 (1H, s, H$_9$); 8.03 (1H, d, J=8.5 Hz, H$_8$); 7.83 (2H, m, H$_{ar\ ortho}$); 7.71 (2H, m, H$_{ar\ meta}$); 6.91 (1H, d, J=85 Hz, H$_7$); 6.19 (1H, dd, J$_1$=10 Hz, J$_2$=5 Hz, H$_2$); 5.81 (1H, d, J=10 Hz, H$_1$); 4.78 (1H, large s, H$_{4a}$); 4.45–4.33 (3H, m, H$_{1'}$, H$_{11\alpha}$); 4.23 (1H, large s, H$_3$); 4.13 (1H, dm, J$_1$=17 Hz, J$_2$=4 Hz, H$_{11\beta}$); 3.97 (3H, s, OCH$_3$); 3.66 (2H, t, J=7 Hz, H$_{10}$); 2.75 (1H, dm, J=16 Hz, H$_{4\alpha}$) 2.23 (2H, m, H$_{12}$); 2.09 (H, dm, J$_1$=16 Hz, J$_2$=5 Hz, H$_3$=2 Hz, H$_{4\beta}$); 1.91 (2H, m, H$_{2'}$); 1.65 (2H, m, H$_{9'}$); 1.41(2H, m, H$_{3'}$); 1.30–1.26 (10H, m, H$_{4'}$, H$_{5'}$, H$_{6'}$, H$_{7'}$, H$_{8'}$).

EXAMPLE 5

10-N-demethyl-10-N-(10'-phthalimidododecyl)-galanthaminium bromohydrate

EXAMPLE 5a

Indirect Synthesis

The reaction is conducted according to the method described in example 2 but using 10-N-demethyl-10-N-(10'-phthalimidododecyl)-galanthamine N-oxide in place of 10-N-demethyl-10-N-(4'-phthalimidobutyl)-galanthamine N-oxide.

EXAMPLE 5b

Direct Synthesis

The sought compound is obtained by working in the same manner as in example 4b but using 10-N-demethyl-10-N-(10'-phthalimidodecy)-galanthamine in place of 10-N-demethyl-10-N-(8'-phthalimidooctyl)-galanthamine (yield 45%).

NMR- $^1$H (300 MHz-CDCl$_3$): 10.17 (1H, s, H$_9$); 8.06 (1H, d, J=8.5 Hz, H$_8$); 7.83 (2H, m, H$_{ar\ ortho}$); 7.71 (2H, m, H$_{ar\ meta}$); 6.91 (1H, d, J=8.5 Hz, H$_7$); 6.19 (1H, dd, J$_1$=10 Hz, J$_2$=5 Hz, H$_2$); 5.81 (1H, d, J=10 Hz, H$_1$); 4.78 Hz(1H, large s, H$_{4a}$); 4.45–4.33 (3H, m, H$_{1'}$, H$_{11\alpha}$); 4.23 (1H, large s, H$_3$); 4.13 (1H, dm, J$_1$=17 Hz, J$_2$=4 Hz, H$_{11\beta}$); 3.97 (3H, s, OCH$_3$); 3.66 (2H, t, J=7 Hz, H$_{10}$); 2.75 (1H, dm, J=16 Hz, H$_{4\alpha}$); 2.23 (2H, m, H$_{12}$); 2.09 (H, dm, J$_1$=16 Hz, J$_2$=5 Hz, J$_3$=2 Hz, H$_{4\beta}$); 1.91 (2H, m, H$_{2'}$); 1.65 (2H, m, H$_{9'}$); 1.41 (2H, m, H$_{3'}$); 1.30–1.26 (10H, m, H$_{4'}$, H$_{5'}$, H$_{6'}$, H$_{7'}$, H$_{8'}$).

EXAMPLE 6

10-N-demethyl-10-N-(12'-phthalimidododecyl)-galanthaminium bromohydrate

EXAMPLE 6a

Indirect Synthesis

The reaction is conducted according to the method described in example 2 but using 10-N-demethyl-10-N-(12'-phthalimidododecyl)-galanthamine N-oxide in place of 10-N-demethyl-10-N-(4'-phthalimidobutyl)-galanthamine N-oxide.

EXAMPLE 6b

Direct Synthesis 13 mg (0.16 mmole, 1.3 eq) of sodium acetate and 63 mg (0.25 mmole, 2 eq) of iodine are added to a solution of 73 mg (0.12 mmole) of 10-N-demethyl-10-N-(12'-phthalimidododecyl)-galanthamine in 5 ml of absolute ethanol. The mixture is heated at reflux under argon for 1 hour. 3 ml of a 10% sodium bisulfite solution is added dropwise at ambient temperature to eliminate the excess iodine. After evaporation of the ethanol, the mixture is taken up again with 30 ml of dichloromethane and washed with 50 ml of water. The organic phase is washed successively with 50 ml of a saturated aqueous solution of sodium carbonate and with 50 ml of a 0.5% hydrobromic acid solution. The organic phase is then dried on sodium sulfate, filtered and evaporated in vacuum. The crude product is chromatographed on a silica column with dichloromethane 80/ ethanol 19/0.5% hydrobromic acid 1 as eluant (yield=28%).

NMR- $^1$H (300 MHz-CDCl$_3$): 10.03 (1H, s, H$_9$); 8.03 (1H, d, J=8.5 Hz, H$_8$); 7.83 (2H, m, H$_{ar\ ortho}$); 7.71 (2H, m, H$_{ar\ meta}$); 6.90 (1H, d, J=8.5 Hz, H$_7$); 6.18 (1H, dd, J$_1$=10 Hz, J$_2$=5 Hz, H$_2$); 5.86 (1H, d, J=10 Hz, H$_1$); 4.78 (1H, large s, H$_{4a}$); 4.47–4.34 (3H, m, H$_{1'}$, H$_{11\alpha}$); 4.22 (1H, large s, H$_3$); 4.18 (1H, dm, J$_1$=17 Hz, J$_2$=4 Hz, H$_{11\beta}$); 3.96 (3H, s, OCH$_3$); 3.66 (2H, t, J=7 Hz, H$_{12'}$); 2.74 (1H, dm, J=16 Hz, H$_{4\alpha}$); 2.39 (1H, large s, OH); 2.23 (2H, m, H$_{12}$); 2.10 (H, dm, J$_1$=16 Hz, J$_2$=5 Hz, J$_3$=2 Hz, H$_{4\beta}$); 1.91 (2H, m, H$_{2'}$); 1.66 (2H, m, H$_{11'}$); 1.40–1.30 (4H, m, H$_{3'}$, H$_{10'}$); 1.23 (12H, large s, H$_{4'}$, H$_{5'}$, H$_{6'}$, H$_{7'}$, H$_{8'}$, H$_{9'}$).

EXAMPLE 7

6-O-demethyl-6-O-(8'phthalimidooctyl)-galanthaminium bromohydrate 13 mg (0.16 mmole, 1.3 eq) of sodium acetate and 62 mg (0.24 mmole, 2 eq) of iodine are added to a solution of 64 mg (0.12 mmole) of 6-O-demethyl-6-O-(8'phthalimidooctyl)-galanthamine in 4 ml of absolute ethanol. The mixture is heated at reflux under argon for 1 hour. 1 ml of a 10% sodium bisulfite solution is added dropwise at ambient temperature to eliminate the excess iodine. After evaporation of the ethanol, the mixture is taken up again in 60 ml of dichloromethane and washed with 50 ml of water. The organic phase is washed successively with 50 ml of a saturated aqueous solution of sodium carbonate and with 50 ml of a 0.5% hydrobromic acid solution. The organic phase is then dried on sodium sulfate, filtered and evaporated in vacuum. The crude product is chromatographed on a silica column with dichloromethane 90/ethanol 9.9/0.5% hydrobromic acid 0.1 as eluant (yield=57%).

NMR- $^1$H (300 MHz-CDCl$_3$+2 drops CD$_3$OD): 9.40 (1H, s, H$_9$); 7.84 (2H, m, H$_{ar\ ortho}$); 7.77 (1H, d, J=9 Hz, H$_8$); 7.73 (2H, m, H$_{ar\ meta}$); 6.96 ($_1$H, d, J=9 Hz, H$_7$); 6.16 (1H, dd, J$_1$=10 Hz, J$_2$=5 Hz, H$_2$); 5.79 (1H, d, J=10 Hz, H$_1$); 4.77 (1H, large s, H$_{4a}$); 4.32 (1H, large t, J$_1$=17 Hz, J$_2$=13 Hz, H$_{11\alpha}$); 4.22 (1H, large t, J=5 Hz, H$_3$); 4.15–4.09 (3H, m, H$_{1'}$, H$_{11\beta}$); 4.02 (3H, s, NCH$_3$); 3.68 (2H, t, J=7 Hz, H$_{8'}$); 2.76 (1H, dm, J=16 Hz, H$_{4\alpha}$); 2.30 (1H, tm, J$_1$=15 Hz, J$_2$=13 Hz, J$_3$=3 Hz, H$_{12\alpha}$); 2.16 (1H, dm, J$_1$=15 Hz, H$_{12\beta}$); 2.10 (1H, dm, J$_1$=16 Hz, J$_2$=5.5 Hz, J$_3$=2 Hz, H$_{4\beta}$); 1.83 (2H, m, J=7 Hz, H$_{2'}$); 1.68 (2H, m, H$_{7'}$); 1.43 (6H, large s, H$_{4'}$, H$_{5'}$, H$_{6'}$).

EXAMPLE 8

6-O-demethyl-6-O-(4'phthalimidobutyl)-galanthaminium bromohydrate

The sought compound is obtained by working in the same manner as in example 7 but using 6-O-demethyl-6-O-

(4'phthalimidobutyl)-galanthmine in place of 6-O-demethyl-6-O-(8'phthalmidooctyl)-galanthamine (yield 55%).

NMR- $^1$H (300 MHz-CDCl$_3$+2 drops CD$_3$OD): 9.40 (1H, s, H$_9$); 7.86 (2H, m, H$_{ar\ ortho}$); 7.77 (1H, d, J=8.5 Hz, H$_8$); 7.73 (2H, m, H$_{ar\ meta}$); 6.97 (1H, d, J=8.5 Hz, H$_7$); 6.19 (1H, dd, J$_1$=10 Hz, J$_2$=5 Hz, H$_2$); 5.78 (1H, d, J$_1$=10 Hz, H$_1$); 4.77 (1H, large s, H$_{4a}$); 4.28 (1H, large t, J$_1$=16.5 Hz, J$_2$=13 Hz, H$_{11\alpha}$); 4.22 (1H, large t, J=5 Hz, H$_3$); 4.14–3.96 (3H, m, H$_{1'}$, H$_{11\beta}$); 4.00 (3H, s, NCH$_3$); 3.76 (2H, t, J=7 Hz, H$_{4'}$); 2.75 (1H, dm, J=16 Hz, H$_{4\alpha}$); 2.29 (1H, dm, J=15 Hz, H$_{12\alpha}$); 2.14 (1h, dm, J=15 Hz, H$_{4\alpha}$); 2.07 (1H, dm, J=16 Hz, H$_{4\beta}$); 1.88 (4H, m, H$_{2'}$, H$_{3'}$).

EXAMPLE 9

6-O-demethyl-6-O-(10'phthalimidodecyl)-galanthaminium bromohydrate

The sought compound is obtained by working in the same manner as in example 7 but using 6-O-demethyl-6-O-(10'phthalimidodecyl)-galanthamine in place of 6-O-demethyl-6-O-(8'phthalimidooctyl)-galanthamine (yield 56%).

NMR- $^1$H (300 MHz-CDCl$_3$+2 drops CD$_3$OD): 9.44 (1H, s, H$_9$); 7.84 (2H, m, H$_{ar\ ortho}$); 7.78 (1H, d, J=8.5 Hz, H$_8$); 7.72 (2H, m, H$_{ar\ meta}$); 6.95 (1H, d, J=8.5 Hz, H$_7$); 6.17 (1H, dd, J$_1$=10 Hz, J$_2$=5 Hz, H$_2$); 5.80 (1H, d, J=10 Hz, H$_1$); 4.77 (1H, large s, H$_{4a}$); 4.33 (1H, large t, J$_1$=17 Hz, J$_2$=13 Hz, H$_{11\alpha}$; 4.22 (1H, large t, J=5 Hz, H$_3$); 4.15–4.02 (3H, m, H$_{1'}$, H$_{11\beta}$); 4.03 (3H, s, NCH$_3$); 3.67 (2H, t, J=7 Hz, H$_{10'}$); 2.74 (1H, dm, J=16 Hz, H$_{4\alpha}$); 2.30 (1H, tm, J$_1$=15 Hz, J$_2$=12 Hz, J$_3$=3 Hz, H$_{12\alpha}$); 2.16 (1H, dm, J$_1$=15 Hz, H$_{12\beta}$); 2.10 (1H, dm, J$_1$=16 Hz, J$_2$=5 Hz, J$_3$=2 Hz, H$_{4\beta}$); 1.83 (2H, m, J=7 Hz, H$_{2'}$); 1.67 (2H, m, H$_{9'}$); 1.42 (2H, m, H$_{3'}$); 1.30 (10H, large s, H$_{4'}$, H$_{5'}$, H$_{6'}$, H$_{7'}$, H$_{8'}$).

EXAMPLE 10

6-O-demethyl-6-O-(12'phthalimidododecyl)-galanthaminium bromohydrate

The sought compound is obtained by working in the same manner as in example 7 but using 6-O-demethyl-6-O-(12'phthalimidododecyl)-galanthamine in place of 6-O-demethyl-6-O-(8'phthalimidooctyl)-galanthamine (yield 58%).

NMR- $^1$H (300 MHz-CDCl$_3$+2 drops CD$_3$OD): 9.46 (1H, s, H$_9$); 7.85 (2H, m, H$_{ar\ ortho}$); 7.76 (1H, d, J=8.5 Hz, H$_8$); 7.73 (2H, m, H$_{ar\ meta}$); 6.95 (1H, d, J=8.5 Hz, H$_7$); 6.18 (1H, dd, J$_1$=10 Hz, J$_2$=4.5 Hz, H$_2$); 5.78 (1H, d, J=10 Hz, H$_1$); 4.75 (1H, large s, H$_{4a}$); 4.31 (1H, large t, J$_1$=17 Hz, J$_2$=13 Hz, H$_{11\alpha}$); 4.22 (1H, large t, J=4.5 Hz, H$_3$); 4.18–4.07 (3H, m, H$_{1'}$, H$_{11\beta}$); 4.03 (3H, s, NCH$_3$); 3.68 (2H, t, J=7 Hz, H$_{12'}$); 2.76 (1H, dm, J=16 Hz, H$_{4\alpha}$); 2.68 (1H, m, H$_{12\alpha}$); 2.28 (1H, dm, J=15 Hz, H$_{12\beta}$); 2.10 (1H, dm, J=16 Hz, H$_{4\beta}$); 1.85 (2H, m, J=7 Hz, H$_{2'}$); 1.68 (2H, m, H$_{11'}$); 1.31 (16H, large s, H$_{3'}$, H$_{4'}$, H$_{5'}$, H$_{6'}$, H$_{7'}$, H$_{8'}$, H$_{9'}$, H$_{10'}$).

EXAMPLE 11

10-N-demethyl-10-N-(6'pyrrolohexyl)-galanthaminium bromohydrate

The reaction is conducted according to the method described in example 1 but using 10-N-demethyl-10-N-(6'-pyrrolohexyl)-galanthamine in place of galanthamine (yield 58%).

NMR- $^1$H (300 MHz-CDCl$_3$): 8.88 (1H, s, H$_9$); 8.86 (1H, large s, NH); 7.59 (1H, d, J=8.5 Hz, H$_8$); 7.23 (2H, t, J=2 Hz, H$_8$,and H$_{11'}$), 7.14 (2H, t, J=2 Hz, H$_{9'}$, H$_{10'}$); 7.00 (1H, d, J=8.5 Hz, H$_7$); 6.13 (1H, dd, J$_1$=10 Hz, J$_2$=5 Hz, H$_2$); 5.58 (1H, d, J=10 Hz, H$_1$); 4.80 (1H, large s, H$_{4a}$); 4.32≧4.23 (2H, m, H$_{1'}$); 4.15 (1H, large t, J=5 Hz, H$_3$); 4.12–4.00 (4H, m, H$_{11}$, H$_6$); 3.99 (3H, s, OCH$_3$); 2.74 (1H, dm, J=16 Hz, H$_{4\alpha}$); 2.28–2.19 (2H, m, H$_{12}$); 2.11 (1H, ddd, J$_1$=16 Hz, J$_2$=5 Hz, J$_3$=2 Hz, H$_{4\beta}$); 2.00–1.88 (2H, m, H$_{5'}$); 1.82–1.68 (2H, m, H$_{2'}$); 1.49–1.36 (4H, m, H$_{4'}$, H$_{3'}$).

By using the procedures indicated above, the following products may be prepared as well which are as well a part of the invention and constitute the preferred products:

| Compound | R—A— | R$_6$ | R$_9$ |
|---|---|---|---|
| B | methyl | H | H |
| C | methyl | methyl | methyl |
| D | pentyl | H | methyl |
| E | octyl | H | H |
| F | decyl | ethyl | H |
| G | aminomethyl | H | H |
| H | aminobutyl | H | H |
| I | aminooctyl | propyl | ethyl |
| J | CH$_3$NH(CH$_2$)$_4$ | H | trifluoromethyl |
| K | C$_2$H$_5$NH(CH$_2$)$_4$ | propyl | hydroxybutyl |
| L | (CH$_3$)$_3$N$^+$(CH$_2$)$_4$ | H | H |
| M | (CH$_3$)$_3$N$^+$(CH$_2$)$_6$ | ethyl | H |
| N | phthalimidobutyl | H | H |
| O | phthalimidohexyl | H | H |
| P | phthalimidodooctyl | H | formyl |
| Q | H | phthalimidobutyl | H |
| R | H | hexyl | acetyl |
| S | phthalimidodecyl | H | H |
| T | phthalimidododecyl | H | methyl |
| U | methyl | phthalimidobutyl | ethoxy |
| V | propyl | phthalimidohexyl | H |
| W | CH$_3$NH(CH$_2$)$_4$ | phthalimidooctyl | allyl |
| X | aminomethyl | phthalimidodecyl | methoxycarbonyl |
| Y | cyanoaminomethyl | aminobutyl | H |
| Z | H | aminomethyl | cyclohexylethyl |
| AA | H | aminooctyl | hydroxymethyl |
| AB | methyl | aminododecyl | H |
| AC | aminodecyl | ethyl | cyanomethyl |
| AD | (1-pyrrolyl)octyl | methyl | H |
| AE | (1-pyrrolyl)butyl | H | aminoethyl |
| AF | benzylaminoethyl | methyl | H |
| AG | (2-MeOC$_6$H$_4$)C$_2$H$_4$ | methyl | H |
| AH | CH$_3$C(O)C$_2$H$_4$ | H | H |
| AI | CH$_3$C(O)C$_3$H$_6$ | methyl | vinyl |
| AJ | methyl | methyl | allyl |
| AK | methyl | methyl | vinyl |
| AL | methyl | methyl | dimethylaminomethyl |
| AM | (CH$_3$)$_3$N$^+$(CH$_2$)$_4$ | methyl | H |
| AN | (CH$_3$)$_3$N$^+$(CH$_2$)$_6$ | methyl | H |
| AO | thioethyl | methyl | H |
| AP | aminoethyl | methyl | H |
| AQ | hydroxyethyl | methyl | H |
| AR | thiopropyl | methyl | H |
| AS | thiobutyl | methyl | H |
| AT | aminopropyl | methyl | H |
| AU | aminobutyl | methyl | H |
| AV | hydroxypropyl | methyl | H |
| AW | hydroxybutyl | methyl | H |
| AX | methyl | methyl | dimethylaminoethyl |
| AY | methyl | methyl | dimethylaminopropyl |
| AZ | methyl | methyl | dimethylaminobutyl |
| BA | methyl | methyl | morpholinoethyl |
| BB | methyl | methyl | trifluoroacetyl |
| BC | phthalimidooctyl | methyl | vinyl |
| BD | phthalimidooctyl | methyl | allyl |
| BE | phthalimidooctyl | H | vinyl |
| BF | phthalimidooctyl | H | allyl |
| BG | phthalimido-oct-4-enyl | methyl | H |
| BH | phthalimido-oct-4-ynyl | methyl | H |

Pharmacological Study of the Products of the Invention

In order to measure the cholinesterase inhibitory activity of the compounds of the invention, the enzymatic activity of acetylcholinesterase is evaluated by the Ellman method (Biochemical Pharmacology, 1961, Vol. 7 pp 88–95, Ellman et al.).

The principle of the method comprises measuring the rate of thiocholine at the time of hydrolysis of the acetylcholine by the enzyme. The hydrolysis is accompanied by a continuous reaction between thiocholine and 5,5'-dithio-2-nitrobenzoic acid (DTNB) which leads to the formation of the yellow colored 5-thio-2-nitrobenzoate anion. The rate of the formation of the anion is measured by absorbance at 412 nm.

The material used is comprised of a 0.1 M (pH 8) phosphate buffer: $Na_2HPO_4/NaH_2PO_4$, an enzyme: acetylcholinesterase from the electrical organ of the electric ray Electrophorus electricus (SIGMA C 2888) purified on Sephadex resin, a substrate: acetylthiocholine iodide 7.5 mM (21.67 mg/10 ml of phosphate buffer) and a reagant: 5,5'-dithio-2-nitrobenzoic acid (DTNB) 10 mM (39.6mg / 10 ml of phosphate buffer).

Thus 3 ml of phosphate buffer, 100 μl of DTNB, 2 μl enzyme, 3.3 μl of the compound according to the invention, and 200 μl of substrate are mixed at 25° C., subsequently the change of absorbance at 412 nm is measured immediately. The results obtained, expressed as inhibitor concentration, are summarized in the table below ($IC_{50}$ represents the inhibitory concentration at 50% activity of the enzyme).

| Example | $IC_{50} \pm SD\ (10^{-7}\ M)$ |
|---|---|
| 1 | 0.8 ± 0.02 |
| 2 | 4.7 ± 0.4 |
| 3 | 0.4 ± 0.01 |
| 4 | 0.1 ± 0.02 |
| 5 | 0.2 ± 0.01 |
| 6 | 1.3 ± 0.09 |
| 7 | 0.7 ± 0.1 |
| 9 | 0.5 ± 0.09 |
| 10 | 3.2 ± 0.9 |
| 11 | 1.7 ± 0.1 |

We claim:

1. A composition having a formula selected from the group

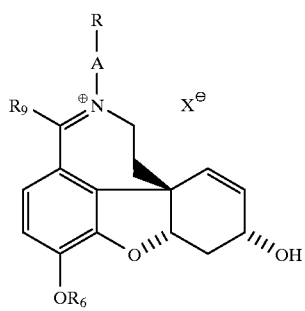

Ia

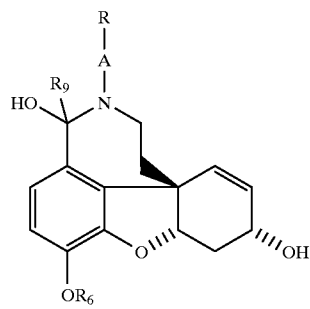

Ib wherein A is optionally unsaturated alkylene of 1 to 12 carbon atoms, R is selected from the group consisting of hydrogen,

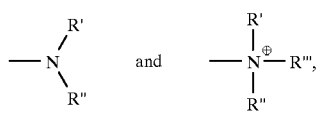

R' and R" are independently selected from the group consisting of hydrogen, cyano, optionally substituted alkyl, optionally substituted aralkyl, optionally substituted aralkenyl, optionally substituted alkylcarbonyl and optionally substituted arylcarbonyl, the optional substituents being at least one member selected from the group consisting of halogen, —OH, —CN, —$NO_2$, —SH, —$NH_2$, mono and dialkylamino, alkoxy, alkylthio, carboxy, salified carboxy, carboxy esterified with a lower alkanol and acyl of an organic carboxylic acid or R' and R" taken together with the nitrogen that they are attached to form a heterocycle selected from the group consisting of pyrrole, imidazole, isothiazole, thiazole, isoxazole, oxazole, pyridine, pyrazine, pyrimidine, pyridazine, indole, isoindole, indazole, quinoline, isoquinoline, phthalazine, quinazoline, pyrrolidine, imidazolidine, pyrrazolidine, piperidine, piperazine, morpholine, thiazolidine and phthalimide, R'" is selected from the group consisting of hydrogen, —CN, optionally substituted alkyl, optionally substituted aralkyl, optionally substituted arylalkenyl, optionally substituted alkylcarbonyl and optionally substituted arylcarbonyl, the optional substituents are as defined above, $R_6$ is hydrogen or —A—R as defined above, $R_9$ is selected from the group consisting of hydrogen, optionally substituted alkyl, optionally substituted alkenyl, optionally substituted cycloalkyl and optionally substituted aryl, the optionally substituents are as defined above, $X^-$ is a pharmaceutically acceptable anion and the non-toxic, pharmaceutically acceptable acid addition salts of Formula Ib.

2. A composition for treating senile dementias comprising an amount of a compound of claim 1 sufficient to treat senile dementias and an inert pharmaceutical carrier.

3. A method of treating senile dementias in humans comprising administering to humans an amount of a compound of claim 1 sufficient to treat senile dementias.

4. A compound of claim 1 wherein
   A is selected from the group consisting of alkylene, alkenylene and alkynylene of up to 8 carbon atoms;
   —CN, alkyl, arylalkyl, arylakenyl,l alkylcarbonyl or arylcarbonyl, the alkyl alkylenyl and aryl substituted by one halo, hydroxy, methoxy, ethoxy, isopropyloxy, tert-butyloxy, methylthio, ethylthio, propylthio, butylthio, pentylthio, formyl, acetyl, propionyl, butyryl, pentanoyl, hexanoyl, acryloyl, crotonyl, benzoyl, free or esterified carboxy, cyano, nitro, mercapto, amino, methylamino, ethylamino, dimethylamino or diethylamino;

$R_6$ is hydrogen or —A—R in which A has the significance of claim 11 and R is hydrogen —NR'R" or —N⊕R'R"R"' in which R' and R" are independently selected from the group consisting of hydrogen, cyano, alkyl, arylalkyl, arylalkenyl, alkylcarbonyl or arylcarbonyl, the alkyl, alkylenyl and aryl optionally substituted by at least one member of the group consisting of halo, hydroxy, methoxy, ethoxy, isopropyloxy, tert-butyloxy, methylthio, ethylthio, propylthio, butylthio, pentylthio, formyl, acetyl, propionyl, butyryl, pentanoyl, hexanoyl, acryloyl, crotonyl, benzoyl, free or esterified carboxy, cyano, nitro, mercapto, methylamino, ethylamino, dimethylamino or diethylamino or R' and R" form together with the nitrogen atom to which they are attached, a member selected from the group consisting of pyrrole imidazole, isothiazole, thiazole, isoxazole, oxazole, pyridine, pyrazine, pyrimidine, pyridazine, indole, isoindole, indazole, quinoline, isoquinoline, phthalazine, quinazoline, pyrrolidine, imidazolidine, pyrrazolidine, piperidine, piperazine, morpholine, thiazoline and phthalimide;

R"' is selected from the group consisting of hydrogen, cyano, alkyl, arylalkyl, arylaklenyl, alkylcarbonyl or arylcarbonyl, the alkyl, alkylenyl and aryl optionally substituted by at least one a member selected from the group consisting of halo, hydroxy, methoxy, ethoxy, isopropyloxy, tert-butyloxy, methylthio, ethylthio, propylthio, butylthio, pentylthio, formyl, acetyl propionyl, butyryl, pentanoyl, hexanoyl, acryloyl,l crotonyl, benzoyl, free or esterified carboxy, cyano, nitro, mercapto, amino, methylamino, ethylamino, dimethylamino and diethylamino;

$R_9$ is selected from the group consisting of hydrogen, alkyl alkenyl, the alkyl and alkenyl being optionally substituted by at least one member of the group consisting of halo, hydroxy, methoxy, ethoxy, isopropyloxy, tert-butyloxy, methylthio, ethylthio, propylthio, butylthio, pentylthio, formyl, acetyl, propionyl, butyryl, pentanoyl, hexanoyl, acryloyl, crotonyl, benzoyl, free or esterified carboxy, cyano, nitro, mercapto, amino, methylamino, ethylamino, dimethylamino, diethylamino radicals or the cyclopropyl, cyclobutyl, cyclohexyl, cycloheptyl, cyclobutene, cyclopentene, cyclohexene, cyclopentanediene, cyclohexadiene radicals, these cyclopropyl, cyclobutyl, cyclopentyl, cyclohexyl, cycloheptyl, cyclobutene, cyclopentene, cyclohexene, cyclopentanediene, and cyclohexadiene radicals optionally substituted themselves by at least one member of the group consisting of halo, hydroxy, methyl, ethyl, propyl, isopropyl, butyl, isobutyl, sec-butyl, tert-butyl, pentyl, isopentyl,l hexyl, isohexyl, vinyl, allyl, propenyl, butenyl, pentenyl, hexenyl, bromoethyl, trifluoromethyl, trifluoroethyl, pentafluoroethyl, methoxy, ethoxy, isopropyloxy, tert-butyloxy, methylthio, ethylthio, propylthio, butylthio, pentylthio, formyl, acetyl, propionyl, butyryl, pentanoyl, hexanoyl, acryloyl, crotonyl, benzoyl, free or esterified carboxy, cyano, nitro, amino, methylamino, ethylamino, dimethylamino and diethylamino.

5. The compound of general formula Ia as claimed in claim 1 and complying to the following formulas:

galanthaminium methanesulfonate;

-10-N-demethyl-10-N-(4'-phthalimidobutyl)-galanthaminium trifluoroacetate;

-10-N-demethyl-10-N-(6'-phthalimidohexyl)-galanthaminium trifluoroacetate;

-10-N-demethyl-10-N-(8'-phthalimidooctyl)-galanthaminium bromohydrate;

-10-N-demethyl-10-N-(10'-phthalimidodecyl)-galathaminium bromohydrate;

-10-N-demethyl-10-N-(12'-phthalimidododecyl)-galathaminium bromohydrate;

-6-O-demethyl-6-O-(8'-phthalimidooctyl)-galathaminium bromohydrate;

-6-O-demethyl-6-O-(4'-phthalimidobutyl)-galathaminium bromohydrate;

-6-O-demethyl-6-O-(10'-phthalimidodecyl)-galathaminium bromohydrate;

-6-O-demethyl-6-O-(12'-phthalimidododecyl)-galathaminium bromohydrate;

-10-N-demethyl-10-N-(6'-pyrrolohexyl)-galathaminium bromohydrate.

* * * * *

UNITED STATES PATENT AND TRADEMARK OFFICE
CERTIFICATE OF CORRECTION

PATENT NO. : 5,958,903
DATED : September 28, 1999
INVENTOR(S) : D. Renko et al.

It is certified that error appears in the above-identified patent and that said Letters Patent is hereby corrected as shown below:

Column 1,
Lines 24-35, replace the existing formula with the following correct formula:

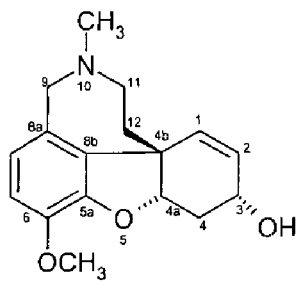

Column 3,
Replace line 34 with the following:
-- triple bond such as ethynyleme or propynylene groups. --

Column 6,
Please define the first formula as -- (1a) -- and please define formula "(Ib)" as -- (1b) --

Column 8,
Please change the title of the formula to read as follows:
-- Reaction Diagram 1. --

Column 10,
Replace the existing formulae with the following correct formulae:

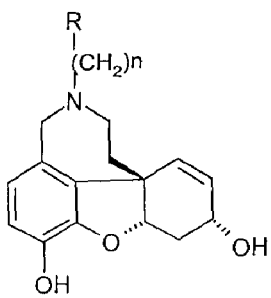

UNITED STATES PATENT AND TRADEMARK OFFICE
CERTIFICATE OF CORRECTION

PATENT NO.   : 5,958,903
DATED        : September 28, 1999
INVENTOR(S)  : D. Renko et al.

It is certified that error appears in the above-identified patent and that said Letters Patent is hereby corrected as shown below:

Column 10 (cont'd),

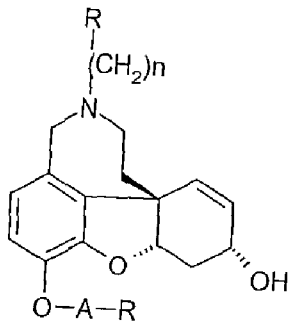

Column 11,
Replace line 18 with the following:
-- Hz, $J_2$ = 3 Hz H $_{2B}$; 1.84 (2H, m, $H_{12}$). --

Column 15,
Replace line 22 with the following sentence:
-- 198 mg (2.40 mmoles, 12 eq) of sodium acetate are added --

Column 23,
Replace line 7 with the following:
-- of claim 1 and R is hydrogen --

Column 24,
Please replace lines 21 and 22 as follows:
-- A compound of claim 1 selected from the group consisting of --
Lines 32, 34, 36, 40 and 44, correct the spelling of -- galanthaminimum --

UNITED STATES PATENT AND TRADEMARK OFFICE
CERTIFICATE OF CORRECTION

PATENT NO. : 5,958,903
DATED : September 28, 1999
INVENTOR(S) : D. Renko et al.

It is certified that error appears in the above-identified patent and that said Letters Patent is hereby corrected as shown below:

Column 24 (cont'd),
Please replace line 41 with the following:
-- 6-0-demethyl-6-0-(12'-phthalimidododecyl)-galanthaminium bromohydrate and; --

Signed and Sealed this

Twelfth Day of April, 2005

JON W. DUDAS
*Director of the United States Patent and Trademark Office*